United States Patent [19]
Litovitz et al.

[11] Patent Number: 5,566,685
[45] Date of Patent: Oct. 22, 1996

[54] PROTECTION OF LIVING SYSTEMS FROM ADVERSE EFFECTS OF ELECTRIC, MAGNETIC AND ELECTROMAGNETIC FIELDS

[75] Inventors: Theodore A. Litovitz, Annapolis; Luis M. Penafiel, Rockville, both of Md.

[73] Assignee: The Catholic University of America, Washington, D.C.

[21] Appl. No.: 265,718

[22] Filed: Jun. 24, 1994

Related U.S. Application Data

[63] Continuation-in-part of Ser. No. 642,417, Jan. 17, 1991, and a continuation-in-part of Ser. No. 88,034, Jul. 6, 1993, Pat. No. 5,450,859, and a continuation-in-part of Ser. No. 107,623, Aug. 18, 1993.

[51] Int. Cl.$^6$ .................................................. A61B 19/00
[52] U.S. Cl. .................................... 128/898; 600/14
[58] Field of Search ....................... 128/897–8; 600/9–15

[56] References Cited

U.S. PATENT DOCUMENTS

| | | |
|---|---|---|
| 4,066,065 | 1/1978 | Kraus . |
| 4,105,017 | 8/1978 | Ryaby et al. . |
| 4,655,898 | 5/1987 | Costa et al. . |

FOREIGN PATENT DOCUMENTS

| | | | |
|---|---|---|---|
| 4101590 | 7/1992 | Germany | 600/9 |
| 2011899 | 7/1992 | WIPO | 600/9 |
| 4011062 | 5/1994 | WIPO | 600/9 |

Primary Examiner—Angela D. Sykes
Assistant Examiner—John P. Lacyk
Attorney, Agent, or Firm—Cushman Darby & Cushman, LLP

[57] ABSTRACT

Methods and apparatus for inhibiting the adverse effect of an ambient time varying field having an electric component and/or a magnetic component on a living system. To provide protection, the field to which the system is exposed is caused to be one wherein at least one of the characteristic parameters of said field to which the living system is exposed is changed within time intervals of less than 10 seconds. Living systems which are benefitted include humans.

2 Claims, 2 Drawing Sheets

GENERATION OF A BIOPROTECTION FIELD WHOSE LEVEL IS A FUNCTION OF THE LOCAL EMF ENVIRONMENT

PROTECTION OF LIVING SYSTEMS FROM ADVERSE EFFECTS OF ELECTRIC, MAGNETIC AND ELECTROMAGNETIC FIELDS

This application is a continuation-in-part of (1) the application of Theodore A. Litovitz, Ser. No. 07/642,417, filed Jan. 17, 1991, pending (2) the application of Theodore A. Litovitz, Ser. No. 08/88034 filed Jul. 6, 1993 now U.S. Pat. 5,450,859 and (3) the application of Theodore A. Litovitz and Luis Miguel Penafiel, Ser. No. 08/107,623 filed Aug. 18, 1993 pending. The inventions described and claimed herein constitute improvements over the inventions described and claimed in the aforesaid applications. The disclosures of the aforesaid applications are included herein by reference. Supporting appendices filed with the aforesaid applications are also included herein by reference. Literature bearing on the need for the inventions of the aforesaid applications and the present application is comprehensively cited in the aforesaid applications and the appendices thereto. The citation of relevant literature is augmented in this specification.

BRIEF SUMMARY OF PRESENT INVENTION

The inventions described and claimed in this application are those wherein the electric, magnetic or electromagnetic field to which a living system, e.g., a human, is exposed is caused to be a bioprotective field. Bioprotective fields are those described in the aforesaid applications in which one or more of the parameters of the field are changed within time periods of 10 seconds or less. The parameters referred to are amplitude, period, phase, waveform and direction. The bioprotective fields inhibit harmful effects on the systems caused by ambient electric, magnetic or electromagnetic fields, e.g., 60 Hz fields to which the living system would otherwise be exposed. Living systems which are benefitted by bioprotective fields include, humans.

The present inventions the strength of the bioprotective field is regulated as a function of the ambient field.

BRIEF DESCRIPTION OF DRAWINGS

Two plots are deemed desirable for an understanding of the present inventions, as well as a circuit for that purpose. These are presented in the drawings which accompany this specification. In these drawings.

DETAILED DESCRIPTION OF PRESENT INVENTIONS

Figure 1:
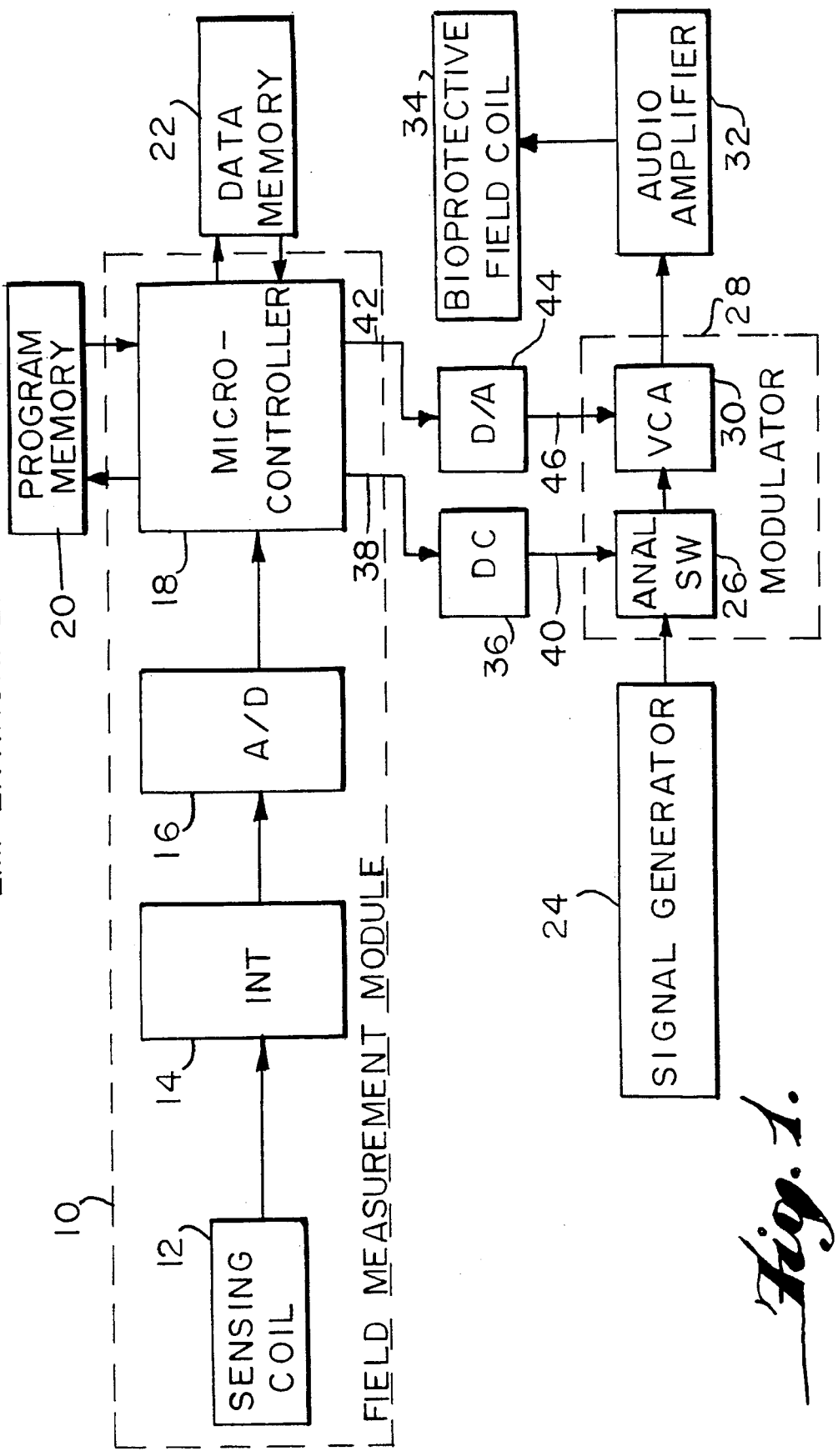
FIG. 1 is a block diagram showing the components of the apparatus that will generate a bioprotective field the strength of which is a function of the local (ambient) EMF.

Relevant literature and studies which augment the disclosure of the aforesaid earlier filed applications will first be set forth as follows:
a. Literature The modern world is heavily dependent on an adequate and continuous supply of electric power. As a consequence, practically every member of our modern society lives in the midst of an electromagnetic field (EMF) rich environment. Delivery of electric power, which is most often in the form of an alternating current, is achieved through extensive distribution networks which are constantly expanding to meet demands. EMFs produced by the flow of electric current through power lines and equipment operating at power line frequencies are referred to as extremely low frequency (ELF) EMFs to distinguish them from higher frequency EMFs such as those resulting from the transmission of telecommunication signals.

The prevalence of ELF EMFs at home, in educational establishments and in the work place, where people spend a great deal of their time, has for the past 10 years fueled considerable interest in scientific research to examine the possibility of adverse health effects from exposure to these fields. At the present time overwhelming evidence exists which shows that a wide range of biological effects are possible even at very low levels of exposure (<5 milligauss–mG). These effects include changes in transcription of specific genes, changes in enzyme activities, production of morphological abnormalities and biochemical modifications in developing chick embryos, stimulation of bone cell growth, suppression of nocturnal melatonin in humans, and alterations in cellular $Ca^{2+}$ pools [Goodman, R., L.-X. Wei, J.-C. Xu, and A. Henderson, "Exposure of human cells to low-frequency electromagnetic fields results in quantitative changes in transcripts", Biochim.

Biophys. Acta, 1009:216–220, 1989; Battini, R., M. G. Monti, M. S. Moruzzi, S. Ferrari, P. Zaniol, and B. Barbiroli, "ELF electromagnetic fields affect gene expression of regenerating rat liver following partial hepatectomy", J. Bioelec. 10:131–139, 1991; Krause, D., W. J. Skowronski, J. M. Mullins, R. M. Nardone, and J. J. Greene "Selective enhancement of gene expression by 60 Hz electromagnetic radiation", in C. T. Brighton and S. R. Pollack, Eds. 'Electromagnetics in Biology and Medicine' (San Francisco Press, Inc., San Francisco, Calif.) pp. 133–138, 1991; Phillips, J. L., W. Haggren, W. J. Thomas, T. Ishida-Jones, and W. R. Adey, "Magnetic field-induced changes in specific gene transcription", Biochim. Biophys. Acta 1132:140–144, 1992; Greene, J. J., S. L. Pearson, W. J. Skowronski, R. M. Nardone, J. M. Mullins, and D. Krause, "Gene-specific modulation of RNA synthesis and degradation by extremely low frequency electromagnetic fields", Cell. Mol. Biol. 39:261–268, 1993; Byus, C. V., R. L. Lundak, R. M. Fletcher, and W. R. Adey, "Alterations in protein kinase activity following exposure of cultured human lymphocytes to modulated microwave fields", Bioelectromag. 5:341–351, 1984; Byus, C. V., S. E. Pieper, and W. R. Adey, "The effects of low-energy 60-Hz environmental electromagnetic fields upon the growth-related enzyme ornithine decarboxylase", Carcinogenesis 8:1385–1389, 1987; Litovitz, T. A., D. Krause, and J. M. Mullins, "Effects of coherence time of the applied magnetic field on ornithine decarboxylase activity", Biochem. Biophys. Res. Commun. 178:862–865, 1991; Litovitz, T. A., D. Krause, M. Penafiel, E. C. Elson, and J. M. Mullins, "The role of coherence time in the effect of microwaves on ornithine decarboxylase", Bioelectromagnetics 14:395–403, 1993; Monti, M. G., L. Pernecco, M. S. Moruzzi, R. Battini, P. Zaniol, and B. Barbiroli, "Effect of ELF pulsed electromagnetic fields on protein kinase C activation process in HL-60 leukemia cells", J. Bioelec. 10:119–130, 1991; Blank, M., "Na K-ATPase function in alternating electric fields", FASEB J. 6:2434–2438, 1992; Delgado, J. M. R., J. Leal, J. L. Monteagudo, and M. G. Garcia, "Embryological changes induced by weak, extremely low frequency electromagnetic fields", J. Anat.

134:533—551, 1992; Juutilainen, J., E. Laara, and K. Saali, "Relationship between field strength and abnormal development in chick embryos exposed to 50 Hz magnetic fields", Int. J. Radiat. Biol. 52:787–793, 1987; Martin, A. H., "Magnetic fields and time dependent effects on development", Bioelectromagnetics 9:393–396, 1988; Aaron, R., D. Ciombor, and G. Jolly, "Stimulation of experimental endochondral ossification by low-energy pulsing electromagnetic fields", J. Bone Mineral Res. 4:227–233, 1989; Bassett, C. A. L., "Beneficial effects of electromagnetic fields", J. Cell. Biochem. 51:387–393, 1993; Ciombor, D. M., and R. K. Aaron, "Influence of electromagnetic fields on endochondral bone formation", J. Cell. Biochem. 52:37–41, 1993; Graham, C., M. R. Cook, H. D. Cohen, D. W. Riffle, S. J. Hoffman, F. J. McClernon, D. Smith, and M. M. Gerkovich, "EMF suppression of nocturnal melatonin in human volunteers", Abstract in the Proceedings of the Department of Energy Contractors Review Meeting October 1993; Wilson B. W., Wright C. W., Morris J. E., Buschbom R. L., and others "Evidence for an effect of ELF electromagnetic fields on human pineal gland function", J. Pineal Res. 9:259–69, 1990; Reiter R. J., Anderson L. E., Busschbom R. L., Wilson B. W., "Reduction of the nocturnal melatonin rise in rats exposed to 60 Hz electric fields in utero and for 23 days after birth", Life Sci. 42:2203–2206, 1988; Bawin, S. M., and W. R. Adey, "Sensitivity of calcium binding in cerebral tissue to weak environmental electric fields oscillating at low frequency", Proc. Natl. Acad. Sci. USA 73:1999–2003, 1976; Bawin, S. M., W. R. Adey, and I. M. Sabbot, "Ionic factors in release of Ca2+ from chicken cerebral tissue by electromagnetic fields", Proc. Natl. Acad. Sci. USA 75:6314–6318, 1978; Blackman, C. F., S. G. Benane, L. S. Kinney, D. E. House, and W. T. Joines, "Effects of ELF fields on calcium-ion efflux from brain tissue, in vitro", Radiat. Res. 92:510–520, 1982; Lindstrom, E., P. Linstrom, A. Berglund, K. H. Mild, and E. Lundgren, "Intracellular calcium oscillations induced in a T-cell line by a weak 50 Hz magnetic field", J. Cell. Physiol. 156:395–398 1993].

Attempts to link the occurrence of biological effects from exposure to ELF EMFs with potential health risks have primarily been made through epidemiclogic studies of selected populations. Some of these studies have demonstrated a small but significant increase in childhood leukemia and other cancers with exposure to ELF EMFs [Wertheimer, N., and E. Leeper, "Electrical wiring configuration and childhood cancer", Am. J. Epidemiol. 109:273–284, 1979; Wertheimer, N., and E. Leeper, "Adult cancer related to electrical wires near the home", Int. J. Epidemiol. 11:345–355, 1982; Savitz, D. A., H. Wachtel, F. A. Barnes, E. M. John, and J. G. Tvrdik, "Case-control study of childhood cancer and exposure to 60-Hz magnetic fields", Am. J. Epidemiol. 128:21–38, 1988]. Although conclusions from epidemiclogic studies can sometimes lead to biased interpretations, the cumulative evidence is suggestive of a positive association between EMF exposure and increased health risk [Bates, M. N., "Extremely low frequency electromagnetic fields and cancer: The epidemiclogic evidence", Environ. Health Perspec. 95:147–156, 1991]. However, in the absence of direct proof, the weight of the epidemiologic data has not been sufficient to quell the controversy about the health risk aspect of EMF exposure. The evidence disclosed in this and the above cited earlier patent applications offers direct proof of health effects from exposure to weak ELF EMFs, and the means to inhibit these effects.

c. Present Inventions

It has been shown in the above cited Litovitz applications and the Litovitz and Penafiel application that the exposure of living systems (inclusive of humans) to EMFs (e.g., 60 Hz fields) can cause harm to the systems, but the harm can be lessened if the field to which the system is exposed is modified by adoption of the bioprotective techniques described in the aforesaid applications. For convenience, these modified fields are being referred to therein as bioprotective fields. By this is meant that the field is one wherein at least one of the characteristic parameters of the field to which the living system is exposed is changed within time intervals of less than 10 seconds. The parameters referred to are amplitude, period, phase, wave form and direction.

The inventions described and claimed herein constitute improvements on the earlier described inventions. The improvements relate to control of the strength of the bioprotective field as a function of the strength of the harmful field to which the living system is otherwise exposed.

An understanding of an exemplary embodiment of the present invention will be aided by reference to FIG. 1 of the aforementioned accompanying drawings.

In FIG. 1 the dash line box 10 contains components for measuring the strength of the harmful EMF existing in the place that the living system is located. Within box 10 is a sensing coil 12 for generating a signal derived from the ambient EMF. This signal is integrated in circuit 14 and then converted to a digital signal in circuit 16. The output of the latter is introduced to a microcontroller 18. The microcontroller 18 is connected with a program memory block 20 and a data memory block 22.

FIG. 1 also shows a signal generator circuit 24, the output of which is conveyed to an analog switch 26 in modulator block 28. The output of the analog switch is conveyed to a voltage controlled amplifier 30. The output of the latter is introduced into an audio amplifier 32, and the signal from it is conveyed to a coil 34 which will produce the bioprotective field to which the living system is to be exposed. Since the bioprotective field is generated by the signal applied to the bioprotective coil 34, the signal is sometimes referred to herein as a bioprotective signal.

FIG. 1 also shows a digital controller 36 which responds to an output 38 of microcontroller 18, and serves via connection 40 to control analog switch 26. Another output 42 of microcontroller 18 serves to convert a digital signal on output 42 to an analog signal in D/A converter 44. The resulting analog signal is applied over connection 46 to the voltage controller amplifier 30.

In operation, by virtue of the components described above, the strength of the signal from generator 24 gated by the analog switch 26, is controlled so that the strength of the bioprotective field from coil 34 is a function of the strength of the ambient EMF detected by the sensing coil 12. In greater detail, the software stored in program memory 20 in part dictates the times when the signal from generator 24 will be gated through analog switch 26. This control of timing comes about by the signal on connection 38 after processing in circuit 36 to operate the analog switch 26 into its respective states. Concurrently, the microcontroller 18 produces a digital signal on connection 42 which is a function of the strength of the EMF that has been detected in the sensing coil 12. After conversion in circuit 44 to an analog signal, the latter, over connection 46, controls the strength of the bioprotective field from coil 34 through the voltage controlled amplifier 30. The arrangement is such that as the strength of the EMF sensed at coil 12 increases, the strength of the bioprotective field will increase.

d. Generation of bioprotection fields

The implementation of the bioprotection field may be accomplished by any of the methods described in the above cited earlier patent applications. Some of these methods are as follows:

Method 1: Modulate an AC current using square wave modulation. That is, interrupt the current delivered to the bioprotection coil at regular intervals. The modulation frequency should be preferably of the order of one second, as guided by the Litovitz inventions. When the modulation frequency is one second the interruption time should be preferably between 0.1 and 0.9 seconds, corresponding to a duty cycle between 10% and 90%. If the local field is measured during the off portion of each cycle, the phase can be adjusted to reduce the local field.

Method 2: Modulate an AC current using DC biased square wave modulation. That is, reduce the current delivered to the bioprotection coil at regular intervals. The modulation frequency and the interval for amplitude reduction should be the same as in 1. The current reduction should be preferably of the order of 50%.

Method 3: Modulate an AC current using frequency modulation of a square wave periodic signal. That is, change the frequency of the current delivered to the bioprotection coil at regular intervals. The period and duty cycle should be same as in 1. The frequency change should be preferably of the order of 10%.

Method 4: Modulate an AC current by periodically changing the wave form. The period and duty cycle should be the same as in Method 1. The wave form change can be for example a shift between a triangular wave form and a sinusoidal wave form.

The AC current referred to in methods 1 through 4 should preferably be of the same order of magnitude as the local environmental EMF emissions.

Method 5: An alternative method to produce a bioprotection signal not involving periodic modulation of an AC current is as follows:

Drive the EMF source with a band-limited noise current with a pass band preferably in the range below 1000 Hz. The noise current may be interrupted in which case the period and duty cycle should preferably conform with the requirements of method 1.

e. Description of common components of typical embodiments of the inventions

It will be understood that the implementation of the bioprotection EMF source with any of the methods previously described may be accomplished using five common components, (1) a low voltage DC power supply, (2) a signal generator, (3) a signal modulator, (4) a power amplifier, and (5) an EMF generating coil. In addition, a magnetic field measurement module with signal control capabilities is needed for situations in which the strength of the bioprotection field is to be controlled as a function of the strength of the local field. Each component may be described as follows:

DC Power supply: The DC power supply is required to power the signal generator, power amplifier and field measurement modules. Each block of FIG. 1 with the exception of the bioprotection and sensing coils is powered by a DC power supply. It can be built using any of several standard methods. Battery powered, AC line transformer isolated, and AC line capacitor coupled DC power supplies are a few standard types. All three types of DC power supplies can be used with the embodiments described herein. Battery operated supplies have a limited interval of operation due to the finite charge capacity of the battery. AC line capacitor coupled DC power supplies can become cumbersome to build when the power requirement is greater than about 150 mA at 5 volts. For long time operation and moderate power requirements the transformer isolated power supply is the preferred choice. One disadvantage is the presence of large EMF's in the vicinity of the transformer. Since these fields are mostly localized, their effect can be minimized by distancing the power supply from the bioprotective coil 34 by the use of a long (e.g., 10 ft) connecting cable. A transformer isolated regulated DC power supply is easily constructed by standard methods using a suitably rated transformer, a half wave or full wave rectifier, a charging capacitor, and a voltage regulator such as one of the LM78XX made by National Semiconductor of Santa Clara, Calif.

Signal generator: The implementation of this component (block 24) depends on the type of signal selected to realize the bioprotection scheme. Two types of practical bioprotection signals are: suitably modulated coherent AC signals, and noise signals.

Coherent signal generator: Coherent signals used to form bioprotection signals to inhibit the biological effects of power line fields should preferably be of frequencies of the same order of magnitude as the power line field. The simplest analog method to generate a 60 Hz (or other power line frequency) field is by means of a transformer. To obtain a clean signal it may be necessary to pass the output of the transformer through a band pass filter. Adjustable low frequency sine wave generators can also be built using operational amplifiers or specialized integrated circuits (ICs) such as the ICL8038 made by Harris Semiconductor of Melbourne, Fla. A different approach to generate as low frequency sine wave is under software control using a microprocessor or a microcontroller. The signal may be produced through the use of an equation, or a look up table containing digitized values of a sampled power line Hz wave form.

Noise signal generator: An alternative method to provide bioprotection from EMFs is using continuous or pulsed noise signals. There are many techniques to generate noise signals. The following methods are suitable for situations in which the overall size of the implementing circuit should be minimized. The timing circuits previously described can be used for pulsed noise.

A noise signal may be generated by amplifying shot noise from a solid state device such as a zener diode. Electric current is defined as the flow of discrete electric charges. Shot noise results from statistic fluctuations of the current due to the finiteness of the charge quantum. The noise generated in this case is white Gaussian noise. An alternative means to produce noise is using digital techniques. A pseudo random digital sequence may be generated using a bank of n shift registers in which the output register is logically combined with one or more previous registers and feedback to the input register. This circuit has been implemented in a special purpose IC, the MM5437 from National Semiconductor of Santa Clara, Calif., which can be used as the noise generator for the applications described herein.

The effectiveness of a bioprotection signal in negating a bioresponse is based on the premise that the biosystem senses the changing characteristics of the bioprotection signal and does not respond. Based on experimental evidence, which is consistent with the dielectric response of biological cells, biosystems are more responsive to ELF fields. Therefore the bioprotection signal is expected to be more effective when operating in the ELF frequency range. Noise generation as described in the previous paragraph results in a wide band signal which must be filtered to produce a signal in the ELF range. Experimental evidence indicates that a noise signal with bandwidth between 30 and 100 Hz can be effective in inhibiting the bioresponse when the rms amplitude of the noise is equal at least one half the rms amplitude of the coherent signal. A band-pass filter may be implemented either with a passive element network or with op-amp based circuits. The op-amp implementation is simpler having less components for an equivalent filter. There are various types of signal filter implementations using op-amps amongst them Butterworth, Chebyshev and Bessel filters. The sharpness of the response may be increased by increasing the number of poles of the transfer function of the filter. A band pass filter formed by cascaded high pass and low pass 2-pole Chebyshev filters with 0.5 dB ripple was found to be one possible adequate implementation for this application.

A noise signal may also be generated digitally under software control using a microprocessor or a microcontroller. The most suitable means to achieve this is using a look up table containing digitized values of a sampled noise wave form.

Signal modulator: With the exception of the continuous noise signal, all other bioprotection signals require periodic changes in properties between one state and another. This involves the use of a signal modulator (block 28) to control the shift between states. In its simplest form the modulator may be a timing circuit which controls an analog switch. There are many possible implementations of such a circuit. One possibility is to use a pulse generator based on an operational amplifier with appropriately selected components to obtain the desired period and duty cycle. Another possibility is to use a monostable multivibrator circuit, for instance, employing a 555 timer. An implementation of this circuit is given in one of the National Semiconductor data books (Special Purpose Linear Devices). The period and duty cycle are easily changed in this circuit in the range 50–100%. The complement of the output signal obtained by means of an inverter such as the DM7404 manufactured by National Semiconductor of Santa Clara, Calif., can be used for values outside this range. The signal modulator may also be implemented using a microprocessor or microcontroller (blocks 18). The timing sequences may be generated using the internal clock of the microprocessor or microcontroller.

The timing scheme is used to operate a module which controls the output of the signal generator. In its simplest form this module is an electronic switch, for instance, a switching transistor, or a digitally controlled analog switch (block 26). The timing sequence may also control the interval during which the field measuring circuitry can perform a measurement. The purpose of making field measurements is to adjust the bioprotection field in response to the measurement. If this function is implemented, the modulation scheme allows adjustment of the level of the bioprotection field and its phase when applicable. The level of the bioprotection signal may be automatically adjusted using a voltage controlled amplifier (VCA, block 30). VCA's may be constructed using operational transconductance amplifiers, for instance the LM13700 made by National Semiconductor of Santa Clara, Calif.

Magnetic field measurement module: Using a feedback scheme the bioprotection signal may be made adaptable to the local EMF environment. Measurement of the local field can be most effectively managed with the use of a microcontroller (block 12) with a multi-channel A/D converter (block 16). A suitable combination would be a digital signal processing microcontroller such as one of the ADSP-2100 series, for instance the ADSP-2101, made by Analog Devices of Norwood, Mass., and a 12 or more bits A/D converter, such as the MAX186 made by Maxim Integrated Products of Sunnyvale, Calif. Since we are primarily concerned with low frequency fields, measurement of the local fields with a microcontroller and A/D converter can be adequately achieved with a sampling rate of 1000 Hz. If it is known that the local field is primarily perpendicular to the plane on which the bioprotective field coil (e.g., coil 34) is to rest, this coil may be used to perform the measurement of the local field. Otherwise, a three dimensional stationary sensing coil (block 12) would be more suitable to perform this measurement.

The sensing coil may be wound on a solid spherical form with three grooves cut at 90 degrees from each other. It should be preferably placed within the bounds of the bioprotection coil, or adjacent to it. Its dimensions should be selected according to performance and functionality. For instance, a sensing coil with a 0.5 inch radius made of 500 to 1000 turns of wire would be suitable for use with a square bioprotection coil of dimensions 26 inches by 20 inches.

The output of the sensing coil is the derivative of the local magnetic field. When the magnetic field is not purely sinusoidal its derivative may have sharp edges which would be difficult to sample accurately. To avoid this potential problem the output of the sensing coil should be integrated (block 14 of FIG. 1) preferably using an integrator based on an operational amplifier. Adequate performance can be obtained when the integration time is of the order of 50 to 100 ms. Measurements of the local field should preferably be performed and stored over an extended interval, for instance, 5 minutes. At the end of the measuring interval the field magnitude calculated as the vector sum of the three perpendicular components should be averaged in order to select the appropriate level of the bioprotection field during the next measuring interval. This choice is based on the fact that the effectiveness of the bioprotection field depends on its magnitude and not its orientation relative to the local field. The controlling signal from the microcontroller used to adjust the output of the bioprotection signal is formed using a digital to analog converter (DAC, block 44 of FIG. 1) for instance, the 8-bit AD557 made by Analog Devices of Norwood, Mass.

Both amplitude and phase information may be obtained from the measurement of the local field. In most cases the local fields are power line fields (60 Hz in the U.S., 50 Hz or other in other countries). For these situations the bioprotection signal may be designed as an interrupted coherent signal with phase opposite to that of the local field, such that it tends to subtract from it during the on portion of the cycle. The measurement of the magnetic field can be performed either continuously as a background operation, or during the off portion of each cycle. When the local field results from multiphase currents the subtraction would be implemented to reduce the largest component. One advantage of this particular implementation is that it provides the bioprotection action while reducing the local EMF environment.

The phase information can be obtained, for instance, by determining the zero crossing times using the sampled data of the local field, and the local field with the superimposed bioprotection field. Synchronization of the bioprotection signal to achieve full or partial cancellation during the on portion of each cycle can be accomplished by shifting the bioprotection field by intervals determined by the internal clock of the microcontroller. Since a microcontroller is used for the field measuring function, the coherent signal could be digitally generated, for instance using a look up table stored in memory.

Use of a microcontroller also allows the possibility of performing a spectral analysis of the local field. In environments in which the local field is not primarily from power line EMFs this analysis would permit discriminating between potentially bioeffecting fields and potentially non-bioeffecting fields based on the frequency of the field.

Power amplifier: In general the output of the signal generator should be amplified in order to drive the EMF coil at the required current level. The current requirements depend on the characteristics of the bioprotection coil. Low power audio amplifiers would be suitable, for instance the LM383, the LM384, or the LM386 manufactured by National Semiconductor of Santa Clara, Calif.

Bioprotection EMF source: In the preferred implementation of the inventions the EMF source, which also may be referred to as the EMF pad, consists of a multi-turn coil of wire (coil 34 of FIG. 1), of dimensions preferably larger than those of the head, embedded between two layers of padding, through which the bioprotection current is made to flow. One example of a bioprotection pad consists of a multi-turn rectangular coil measuring 26"×20", embedded within a standard size pillow. This "pillow" EMF pad will provide protection to the user while asleep or at rest with minimal interference of normal routine. If firm pillows are used the center of the head should be located an average of 7" away from the plane of the coil. The magnetic field generated by this coil can be calculated by adding up all contributions from infinitesimal current elements along the entire loop. For the purpose of determining the range of exposure levels from this coil we assume that the sensitive regions of the head are located within a volume enclosed by a 22"×16"×4" parallelepiped resting on a plane 5" above the plane of the coil and centered directly over the coil. The magnetic field inside this volume varies within ±45% of the average of the maximum and minimum fields. For instance, if the axial field on the plane of the coil is 20 mG, the field variation inside the specified volume would be between approximately 4 mG and 13 mG. To achieve optimum inhibition the EMF pad should be positioned such that bioprotection field from the coil in the region of interest is at least one half the level of the coherent field within the same region. If an interrupted signal is used the amplitude requirement applies to the "on" portion of each cycle.

f. Relationship of fields

Figure 2:
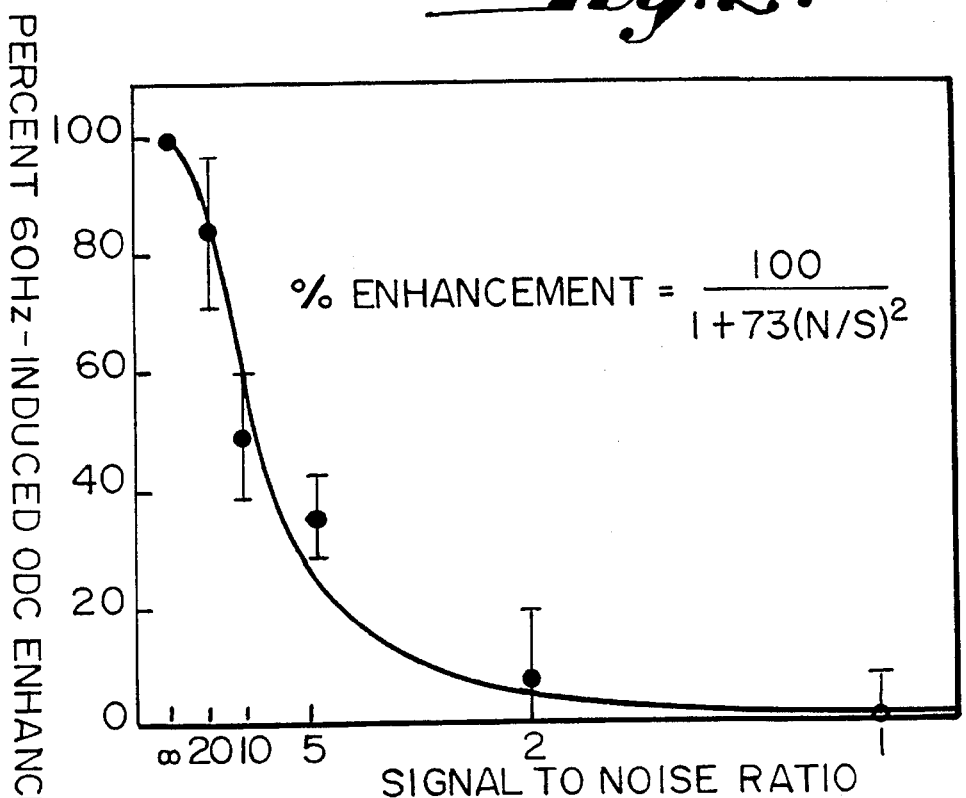
FIG. 2 plots the enhancement of ODC activity in L929 cells simultaneously exposed to 60-Hz and noise EM fields.
Figure 3:
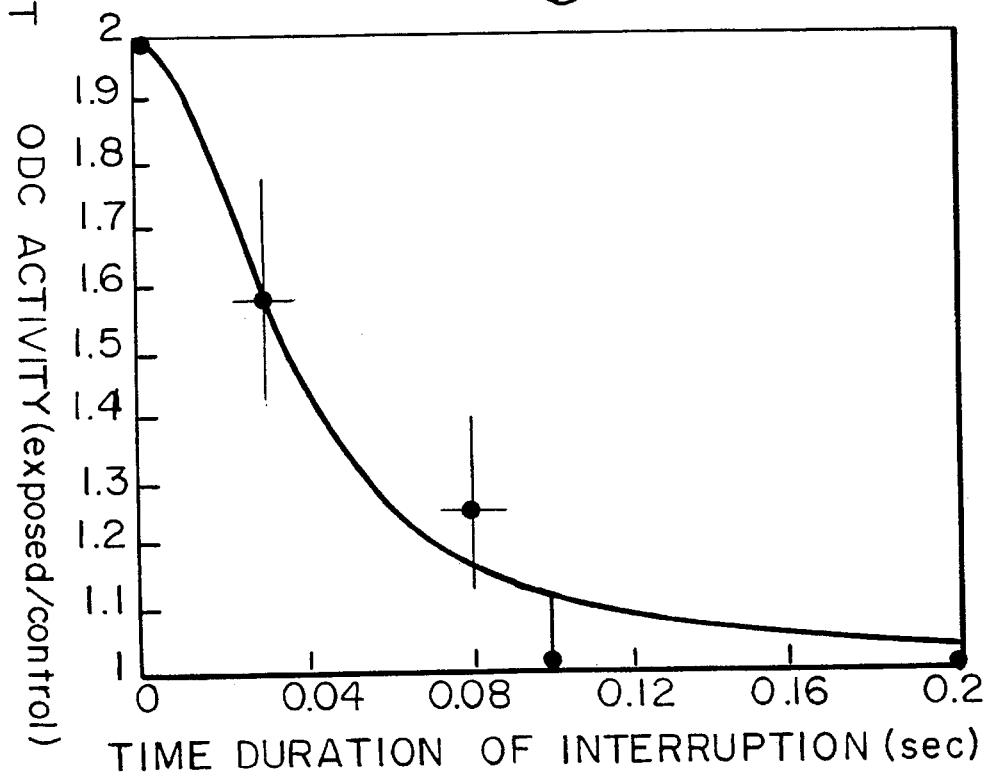
FIG. 3 plots the ODC activity in murine L929 cells induced by a 4-h exposure to a 100 mG field as a function of a duration of the once-per-second interruption time during which the field is off.

The investigations to date show that the effectiveness of the inhibition of biological effects by superposition of bioprotection fields is dependent upon the relative strength of the bioprotection and coherent (e.g., power line) fields. As an example, FIG. 2 shows enhancement of ODC activity in L929 cells simultaneously exposed to a 60 Hz field and a bioprotection field implemented as a noise field. From this figure it can be concluded that full inhibition is achieved when the signal to noise ratio is equal to 1, that is, when the strengths of the bioprotection and coherent fields are equivalent. Significant inhibition levels are obtained at higher signal to noise ratios. For instance, when the signal to noise ratio is equal to 2 the inhibition level is 95%, and when the signal to noise ratio is equal to 5 the inhibition level is 75%. The inhibition level is calculated as 100 minus the percent enhancement such that a percent enhancement of 100 corresponds to 0% inhibition and a percent enhancement of 0 corresponds to 100% inhibition. Other investigations relating to the measurement of the averaging time over which biological cells determine the characteristics of an externally imposed electromagnetic field reveal the necessary conditions for interrupting a coherent signal to achieve bioprotection effects. FIG. 3 shows the results of one of these investigations. In this figure ODC activity ratio of 1 corresponds to full inhibition and ODC activity ratio of 2 corresponds to no inhibition. From this figure it can be concluded that full inhibition can be achieved when the time duration of interruption is 0.2 seconds during successive one second intervals. Partial inhibition can be achieved when the interruption time is lower than 0.2 seconds. For instance, the inhibition level is 90% when the interruption time is 0.1 seconds, and 80% when the interruption time is 0.08 seconds.

The foregoing experimental results provide guidelines for the design of bioprotection fields for general applications. In view of these results the preferred specifications of the bioprotection field are that its amplitude be equal to or greater than the local coherent field (e.g., a power line field), and that the interruption rate for interrupted signals with 1 second period be preferably between 0.2 and 0.8 seconds. When the bioprotection field does not subtract from the local field it may be desirable to minimize the effect of the superimposed field on the strength of the local field. In this case it is necessary to minimize the on time and the amplitude of the bioprotection signal while maintaining its inhibition characteristics. A compromise must be drawn in situations such as this one. An acceptable configuration is to set the on time to 0.15 seconds on successive 1 second periods, and set the field strength to 50% of the field strength of the local field. In most practical applications of the present inventions the local fields will be below 20 mG. For these cases the strength of the bioprotection field would be set to below 10 mG with an on 0.15 seconds in successive one second intervals. With these specifications the average strength of the superimposed bioprotection field during each period is less than 1.5 mG. The average strength is calculated by multiplying the field strength during the on portion of each cycle time the fraction of time that the field is on during each cycle.

What is now claimed is:

1. A method of inhibiting the adverse effects of an electromagnetic field on living systems, which method includes the step of measuring the strength of the electromagnetic field to which the living system would be exposed, the step of generating a bioprotection field to which the living system is to be exposed, and the step of controlling the strength of the bioprotection field as a function of the measured strength of the electromagnetic field.

2. An apparatus for inhibiting the adverse effects of an electromagnetic field on living systems, which includes means for measuring the strength of the electromagnetic field to which the living system would be exposed, means for generating a bioprotective field to which the system is to be exposed, and means for controlling the strength of the bioprotection field as a function of the measured strength of the electromagnetic field.

* * * * *